United States Patent
Hale (10) Patent No.: US 10,500,009 B1
(45) Date of Patent: Dec. 10, 2019

(54) DISPOSABLE MEDICAL DRAPE

(71) Applicant: Protection Products, Inc., Hickory, NC (US)

(72) Inventor: Jeffrey Wayne Hale, Hickory, NC (US)

(73) Assignee: Protection Products, Inc., Hickory, NC (US)

(*) Notice: Subject to any disclaimer, the term of this patent is extended or adjusted under 35 U.S.C. 154(b) by 2 days.

(21) Appl. No.: 15/702,678

(22) Filed: Sep. 12, 2017

Related U.S. Application Data (60) Provisional application No. 62/518,066, filed on Jun. 12, 2017, provisional application No. 62/393,487, filed on Sep. 12, 2016.

(51) Int. Cl.

| | |
|---|---|
| *B32B 7/02* | (2019.01) |
| *A61B 46/10* | (2016.01) |
| *A61B 46/00* | (2016.01) |
| *A61G 13/10* | (2006.01) |
| *B32B 7/12* | (2006.01) |
| *B32B 27/10* | (2006.01) |
| *B32B 27/12* | (2006.01) |
| *B32B 27/32* | (2006.01) |
| *B32B 5/02* | (2006.01) |

(52) U.S. Cl.
CPC .............. *A61B 46/10* (2016.02); *A61B 46/40* (2016.02); *A61G 13/101* (2013.01); *B32B 5/022* (2013.01); *B32B 7/12* (2013.01); *B32B 27/10* (2013.01); *B32B 27/12* (2013.01); *B32B 27/32* (2013.01); *B32B 2262/0253* (2013.01); *B32B 2307/726* (2013.01); *B32B 2307/7265* (2013.01); *B32B 2535/00* (2013.01)

(58) Field of Classification Search
CPC ............................... A61F 5/3707; A61L 15/00
See application file for complete search history.

(56) References Cited

U.S. PATENT DOCUMENTS

| | | | |
|---|---|---|---|
| 3,650,267 A | 3/1972 | Anderson | 128/132 |
| 3,667,458 A | 6/1972 | Krebs | 128/132 |
| 4,923,453 A | 5/1990 | Bullard, Jr. | 604/356 |
| 5,156,167 A | 10/1992 | Busch | 128/852 |
| 5,713,372 A | 2/1998 | Pinney et al. | 128/855 |
| 5,845,641 A | 12/1998 | Pinney et al. | 128/849 |
| 2015/0272771 A1* | 10/2015 | O'Brien | A61F 5/3707 |
| | | | 128/847 |

FOREIGN PATENT DOCUMENTS

| | | | |
|---|---|---|---|
| CN | 204468305 | 7/2015 | A61B 19/08 |

* cited by examiner

*Primary Examiner* — Lawrence D Ferguson
(74) *Attorney, Agent, or Firm* — MacCord Mason PLLC (57) ABSTRACT

Self-clamping drape systems, apparatuses, kits and methods are shown and described. End drape systems, apparatuses, kits and methods are shown and described. A disposable medical drape may include a drape and a self-clamping system. A disposable medical drape system may include a drape, a self-clamping system and one or more end drapes. A self-clamping drape may have attached clamps and/or be secured by way of self-clamping clamps. The medical drape system may form a barrier beneath a medical operating room table.

16 Claims, 9 Drawing Sheets

DISPOSABLE MEDICAL DRAPE

FIELD

The present invention relates generally to disposable medical drapes and, more particularly, to systems, apparatus, kits and methods for disposable, self-clamping and accessory medical drapes/sheets for medical tables, equipment and personnel in medical situations, for example, in emergency room, hospitals and surgical procedures, and for draping any equipment for sterilization and prevention of cross-contamination requirements.

BACKGROUND

Advances in medical science have brought technological improvement and more sophisticated equipment into the medical setting. By way of example, many medical tables in use today in operating and emergency rooms are highly mechanized and adaptable to many different needs and scenarios. These tables are quite expensive, and while solving many medical needs, challenges, recognized by Applicant, have arisen to prevent contamination of such equipment, which must then be taken out of use for extensive, time consuming and meticulous decontamination. Cross-contamination in the medical setting is of major concern.

Preventing contamination of equipment and exposure of personnel has long been a concern in the medical field, particularly in surgical and emergency room procedures where blood, body fluids, medications and irrigation fluids can quickly accumulate to produce large amounts of fluids that are released and difficult to retain. During intense medical treatment, for example in high trauma situations, the doctors and medical staff should be able to focus on the patient and not be expected to turn their focus to clean-up and control of the possibly contaminating fluids during the patient's treatment. In certain injuries, such as injuries to the head, chest and abdomen, higher than average amounts of blood and irrigation fluids may be discharged, compounding the contamination and fluid control problem. In other scenarios, specialty equipment, such as highly mechanical tables and/or the underpinnings of surgical tables are prone to contamination during procedures. Still in other examples, medical equipment that may be susceptible to frequent patient interaction, such as a patient pushing an I.V. stand and/or railings on patient beds, may be prone to contamination. Issues with health, contamination, cross-contamination and safety are of major concern, especially in these types of situations. Clean up and decontamination of medical equipment can be time-consuming, costly and may take needed medical supplies out of service for unacceptable amounts of time. In addressing these issues, however, ease of use and accessibility must remain high as contamination issues are addressed. These concerns are also balanced with the economics involved with providing a solution, as many alternatives are cost prohibitive in hospital, medical and first responder scenarios.

Therefore, Applicant desires an economical self-drape system, apparatuses, kits and methods that provide better management of protection against contamination in medical situations to minimize contamination, clean-up and safety concerns.

SUMMARY

In accordance with the present disclosure, self-clamping drapes, drape systems, kits and methods are provided for containing waste fluids and the like and preventing contamination. This disclosure provides improved drapes, kits, assemblies and methods that are convenient, efficient, and safe for the user.

A drape for containment of medical waste fluids may include a body portion, a first side portion, a second side portion, a first end, and a second end. There may be at least one clamp attached to the drape.

In other embodiments, a drape may include a top surface, a bottom surface, a first end, and a second end. The drape may be configured to form a perimeter around an irregular surface. A clamping system may be included with the drape to secure the drape around the irregular surface. The clamping system may be maintained between a clamped and a non-clamped position. The drape may include a clamping system. The clamping system may secure the drape around a circular base.

One embodiment includes at least one end drape. The end drape may be a drape for covering an end of a medical table along its base and/or along the surrounding floor. The end drape may be an accessory drape that, along with the drape, forms a drape kit. A drape kit may include a drape for covering a base, a clamping system and a set of end drapes.

Methods for a clamping drape system are also included. A method for covering a medical table base may include covering the base with drape and clamping the drape into place with self-clamping clamps.

A drape clamping kit is included within the scope of this disclosure and may include any of the embodiments described herein.

These and other aspects of the inventions of the present disclosure will become apparent to those skilled in the art after a reading of the following description of the preferred embodiment when considered with the drawings.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of example Embodiments along with a review of the drawings, in which.

DESCRIPTION OF EMBODIMENTS

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 1:
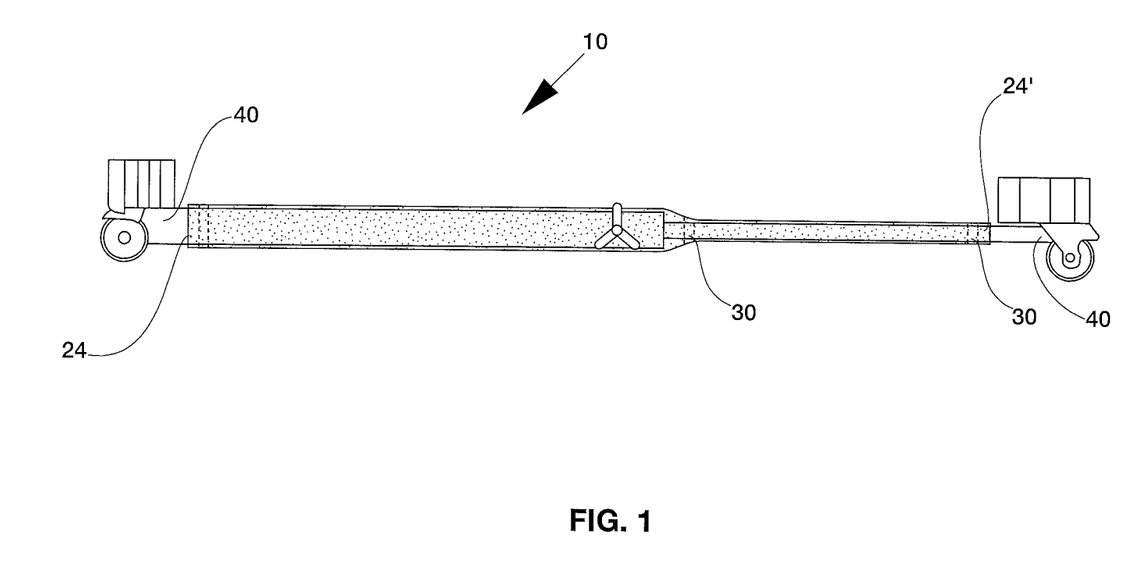
FIG. 1 is a side view of one example of a clamped drape according to the present disclosure.
Figure 2:
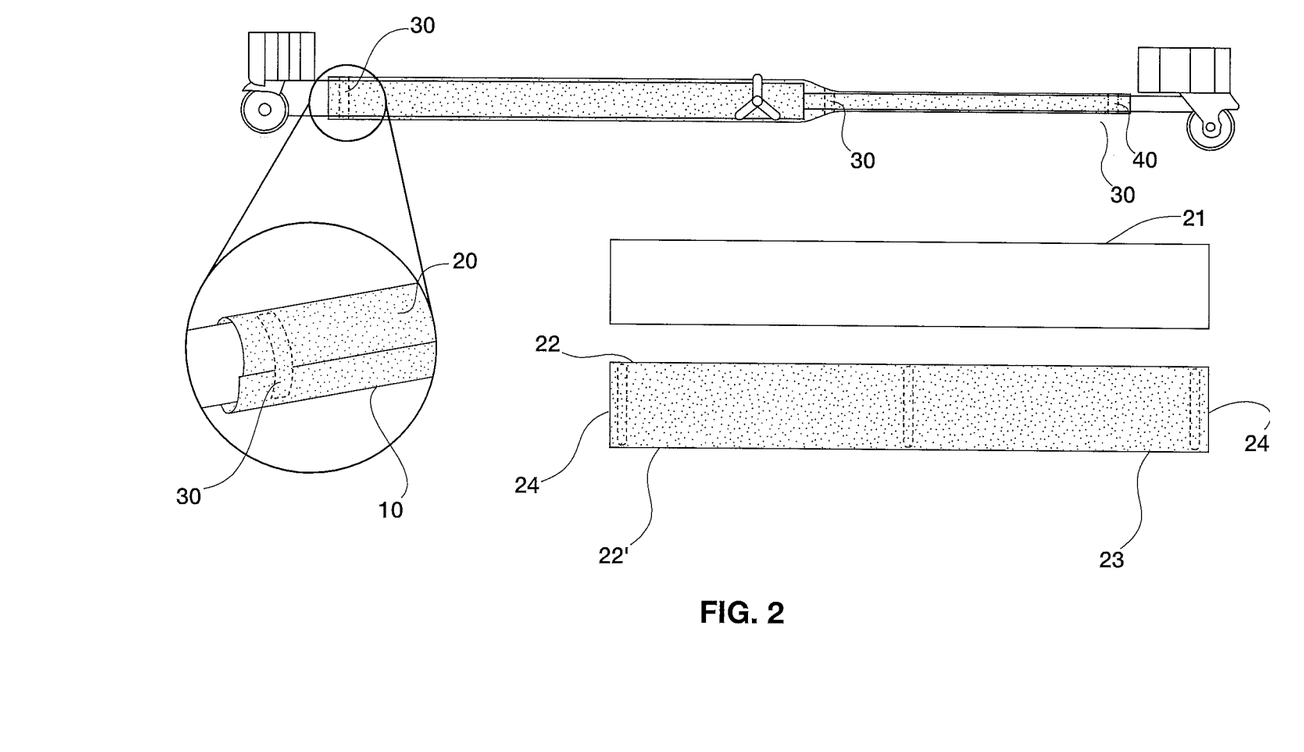
FIG. 2 is an exploded view of the drape of FIG. 1 and one example of a drape according to the present disclosure in a non-clamped, flat position.

Referring now to the drawings in general and FIG. 1 in particular, it will be understood that the illustrations are for the purpose of describing embodiments of the disclosure and are not intended to limit the disclosure or any invention thereto.

There are many needs in healthcare applications for quick, simple and secure attachments of flexible protective materials to round and irregular surfaces. Securing these protective materials through Applicant's drape provides many benefits to the healthcare system, including, reduced risk of infection, reduced risk of cross contamination, reduced risk to workers, improved efficacy in disinfection of reused equipment, reduced cost to the healthcare system and improved efficiencies. Also, the invention as disclosed has broader applications throughout the healthcare system when applied to a variety of reused medical equipment such as IV Poles, Ambulation Aids, Surgical Microscopes, Surgical and Radiological Imaging Equipment, Laboratory and Diagnostic equipment and patient transport equipment, etc.

Applicant's inventions of the present disclosure allow safe, rapid and efficient application of flexible materials to this type of medical equipment to protect items from becoming contaminated with fluid borne and contact contaminants In the healthcare setting, much time and effort is devoted to prevent cross patient contamination, and also, prevention of infecting staff with pathogens carried by patients. As such, Applicants invention may be impervious to fluids and in some cases both impervious to fluid and also absorbent to catch and contain fluid. In many cases, the surfaces to protect are not easily draped, and in many cases, adhering a protective material to them is extremely challenging, as the surfaces to protect may be circular, cylindrical, hexagonal, vertical, angular and irregular. Conventionally, materials are applied to these challenging surfaces with some form of adhesive or, may even be just draped over the medical equipment. Applicant recognized there are shortcomings to these approaches. Some of the shortcomings of these common attachments are: difficulty in maintaining a secure attachment, residual adhesive residue, time consuming attachment, and inflexibility of fixed attachment points. Applicant's approach addresses all of these shortcomings and provides a fast and simple means for protecting such equipment.

Expected applications for attachment, by way of example, for the inventions of the present disclosure include, but are not limited to, IV Administration Stations and Poles, Specialized Surgical Equipment, Ambulation and Ambulatory Equipment, Patient Transfer Equipment and Laboratory Devices and Instruments.

FIG. 1 shows a side view of examples of a self-clamping drape, generally designated 10, according to the present disclosure. The drape 10, for preventing contamination by medical waste fluids, may include in some embodiments, a front surface 21 and a back surface 23, a drape body 20, a first side portion 22 and a second side portion 22'. The drape 10 may also include a first end 24 and a second end 24'. The self-clamping drape 10 may be applied to cover irregularly shaped medical equipment and self-maintain a clamped position of the drape onto the medical equipment.

Also included with drape 10 may be one or more clamps 30. In some examples, drape 10 may include one clamp, two clamps, three clamps, four clamps, etc. Clamps 30 may be, for example, attached to, adjoined with, imbedded in, and/or included with drape 30. In some examples, clamps 30 may be attached to drape 10 with adhesive (for example adhesive glue and/or adhesive tape) and/or sewn into drape 10. One or more clamps 30 may accompany the drape 10 and be administered over the drape once the drape is placed over the item to be protected.

Figure 3:
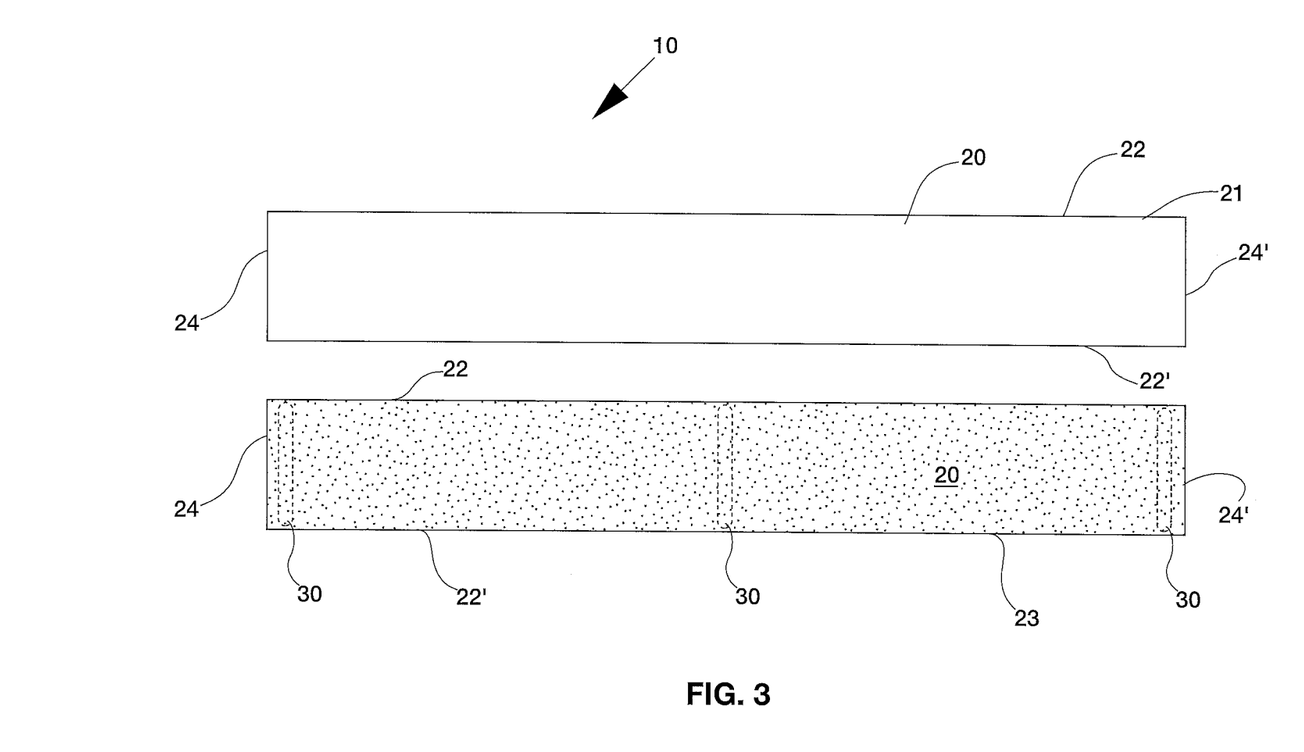
FIG. 3 is a bottom view and top view of one example of a drape in a non-clamped state according to the present disclosure.

Clamp 30 may be a quick convert clamp. Clamp 30 may, in some embodiments, alternate between a clamped and a non-clamped positions. Clamp 30 may be on the front surface 21, the back surface 23 and/or contained within drape 10. The clamp may in a non-clamped position be substantially linear and/or in a position such that the clamp ends extend distally away from each other. The clamp in the clamped position may be biased in a curved position and/or in a position where the clamp ends move toward each other. In the clamped position, the clamp ends may overlap. The clamp may, in a non-clamped position, retain a substantially linear position (as seen in FIG. 3) while in the clamped position, clamp 30 may retain an inwardly curved positon (as seen in FIG. 1). The clamp 30 may alternate between clamped and non-clamped positions when biased toward either position. The clamp 30 may extend at its length between drape side 22 toward side 22'. In other embodiments, clamp 30 may extend across the body 20 of the drape at other angles either side 22 to 22', end 24 to end 24', and/or side 22, 22' to end 24, 24' and/or in any direction that allows the clamp to secure the drape to the medical equipment.

Figure 4:
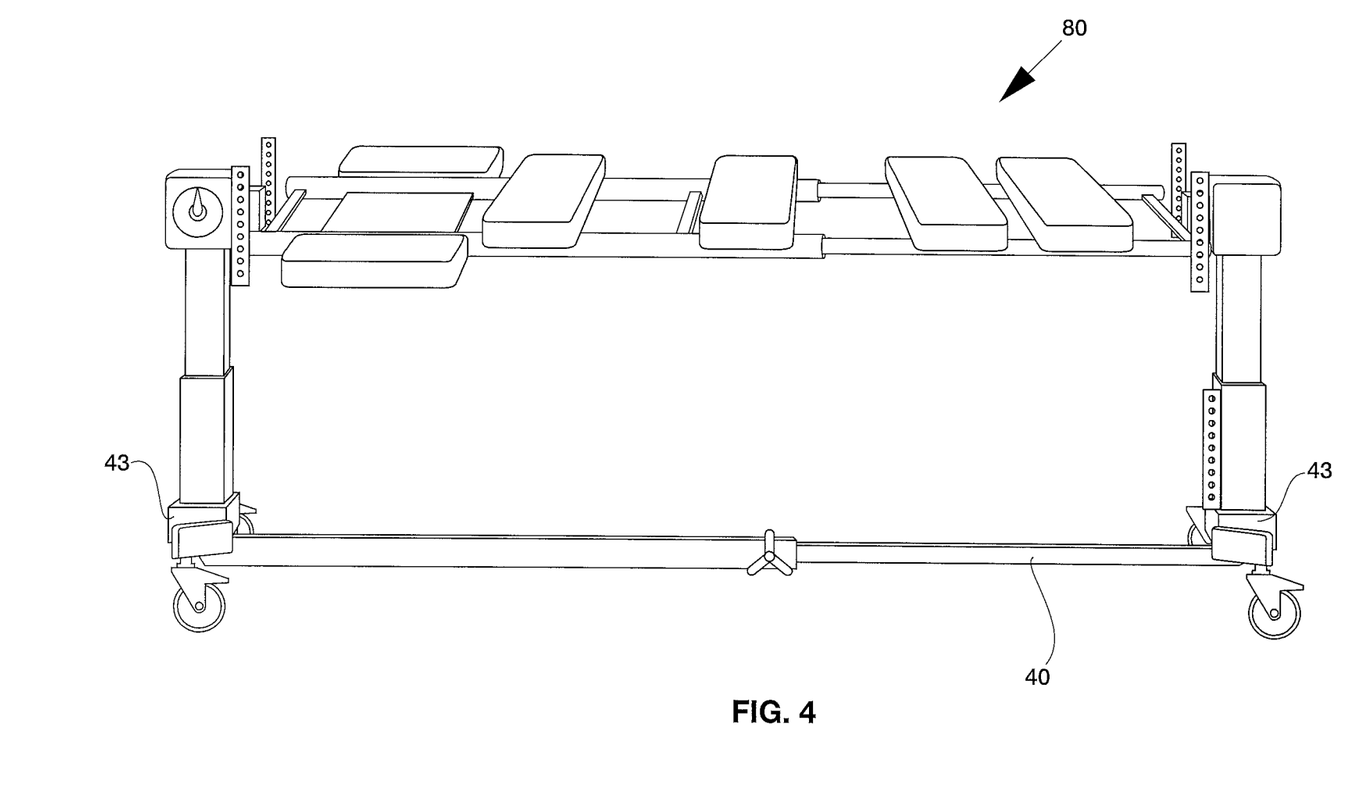
FIG. 4 is a side view of one example of a medical table on which the drape of the present disclosure may be clamped.

The dimensions of the drape 10 may be variable according to the equipment dimensions on which the drape is intended for use. The drape 10 is able to cover otherwise hard to cover areas, for example, curved areas of equipment, difficult to reach areas of equipment and frequently left uncovered areas of medical equipment. In one example, drape 10 may be intended for use on a table base, such as a base 40 of a Jackson table, one example as shown in FIG. 4. Base 40 may remain exposed in many conventional situations because the head support, thigh pads and support sections of such a table are each respectively covered. However, Applicant realizes that in many instances, the covers for the supports do not prevent contamination of lower table parts, such as base 40.

In use, as for example with base 40, drape 10 may be strewn across base 40, in some examples, in a substantially non-clamped position. Once the length of the base 40 is covered by drape 10, the user applies a pressure to each clamp 30. The pressure biases the clamp inward toward itself and the clamp, for example, "slaps" and/or "snaps" into a curved biased-maintained position that clamps the drape to and around the equipment, here in this example, the base 40. The drape 10 may be extended from one end of the base to the other end of the base and each clamp clamped as the drape is extended to cover the base 40. If the drape is too long for the length of the base 40, the drape may be doubled-back upon itself to the desired length and the clamp clamped over the doubled-back drape portion to secure the drape in the shortened length on the base 40. Once the medical procedure is completed, the drape may be pulled at one side to activate a release of the base 40 by drape 10 by uncurling the clamps 30, either partially or completely.

When uncurled completely, clamps 30 are able to maintain the alternate substantially linear position. The drape 10 is then disposed of and the base 40 remains free of contamination.

One embodiment may include a clamping system. In one example, quick convert clamps may be included with the drape. Clamps 30 may range, by way of example, from about 6" to about 11" and secure materials in the about 7" to about 14" range. Additionally, applications for protecting commonly touched or handled equipment such as IV Stations and Poles may require smaller sizing and in some cases a vertical application. In this use, the convertible clamps may be in the about 2" to about 7" range. In this example, the drape 10 may, in use, be applied to an I.V. stand tube to protect from cross-contamination areas of the tube often touched my patients. In other embodiments, the drape 10 may be sized to be applied to the hand rails on a patient bed. The clamping system may include at least one end clamp for clamping one end of a drape, a second end clamp for clamping a second opposite end of the drape and one middle clamp for securing and clamping the drape at a point, around the mid-point by way of example, in the middle between the two end clamps.

In some examples, a drape 10 may include between 2 and 8 clamps. The clamps 30 may be integrated into or with the protective material. In some applications the clamps 30 will be adhered to protective material and in others these clamps will be integrated into the material itself.

The drape body 20 may include an impervious layer. In some examples, drape 10 may be formed of layers. An impervious layer may form all or a portion of the bottom surface as a backing with an absorbent material layer forming all or a portion of the top surface. In embodiments with a bottom impervious layer and an absorbent top layer, it is desirable for the drape to be flexible enough to allow for attachment of other technical or mechanical fixtures, such as for example, surgical rail clamps and/or arm boards. Typically such fixtures attach over the drape so an opening in the drape does not allow waste fluid to migrate through the opening to contaminate the underside and the table. The drape 10 is also flexible enough to fit over and accommodate irregular shapes, for example knobs and/or screws, along the base 40 and the clamps 30 allow for accommodation of irregular shaping when securing the drape to the base.

In some examples, the layers of the drape 10 may include a polyethylene layer, at least one layer of wood paper, a layer of polypropylene non-woven and a glue, such as a hot melt glue. In other examples, the layers of the drape 10 may include a layer of polyethylene, a layer of non-dust air laid paper, a layer of thermal bonding non-woven polypropylene and an adhesive. Plastics, non-wovens and combinations for use in the drapes are also considered within the scope of this disclosure.

Superabsorbent polymer may be included in the drape 10. In some examples, superabsorbent polymer may extend along the central portion of drape body, in some instances, from a substantial part of the central portion from end to end.

Lengths and widths are exemplary and other dimensions are considered within the scope of this disclosure.

Attachment of the clamps 30 to drape 10 may, for example, be with any attachment securing structures, for example, hook and eye closures, buttons, fixed stitching, gluing, glue dots, strip adhesives, Velcro, buttons, binders, clips, clamps, drawstrings, and or hook and loop. Clamps 30 may take on any various shape, for example, strips or circles, may be square, oval, rectangular, linear, etc.

Figure 5:
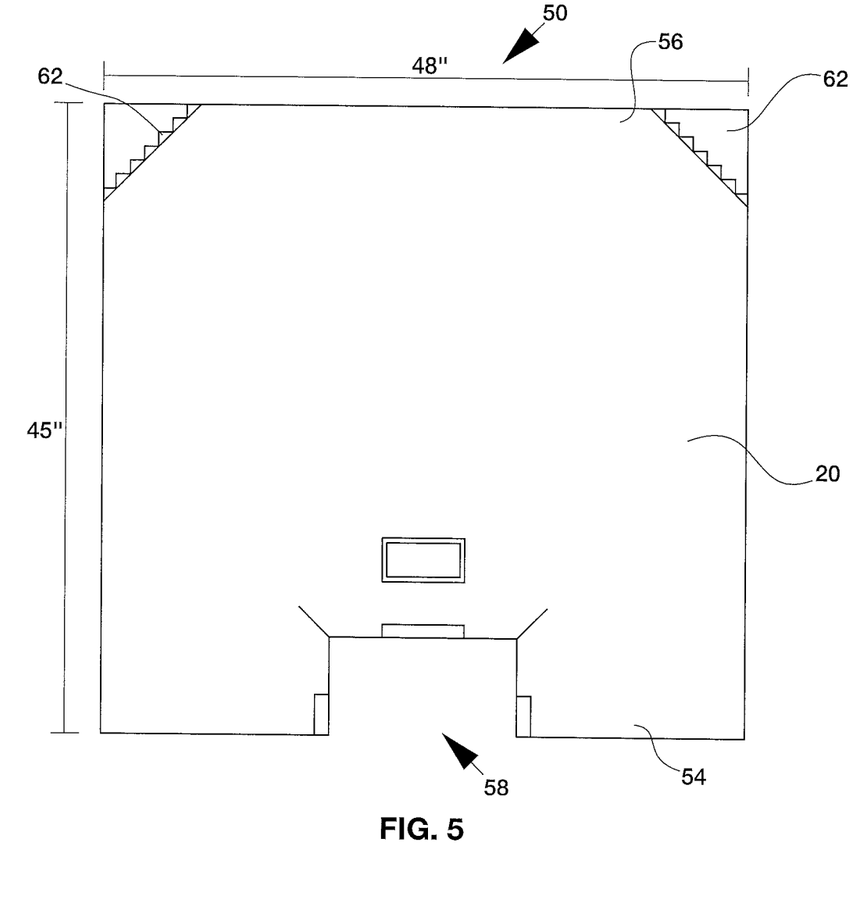
FIG. 5 is a top view of one example of an end drape according to the present disclosure.
Figure 6:
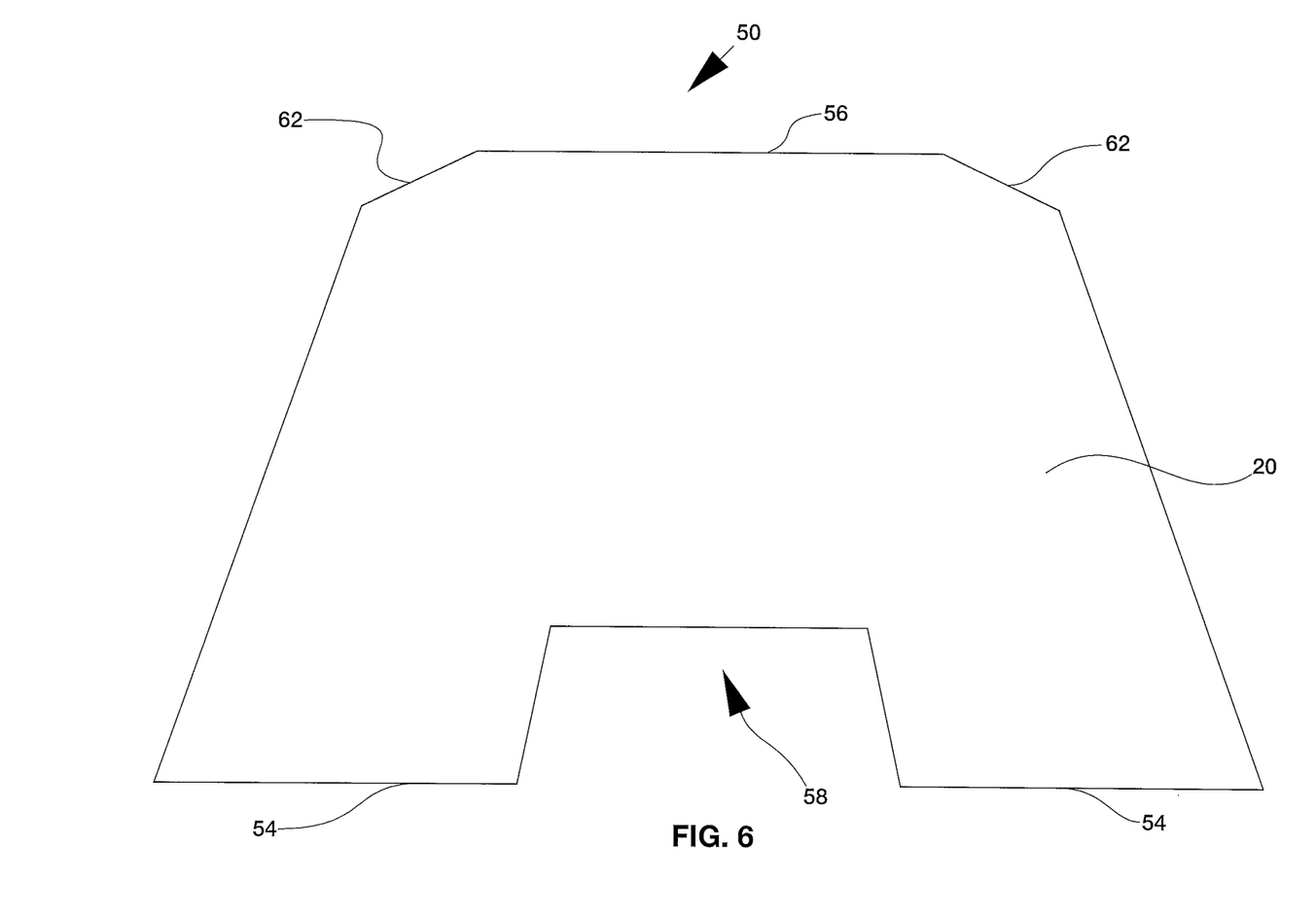
FIG. 6 is a top perspective view of one example of the end drape of FIG. 5.
Figure 7:
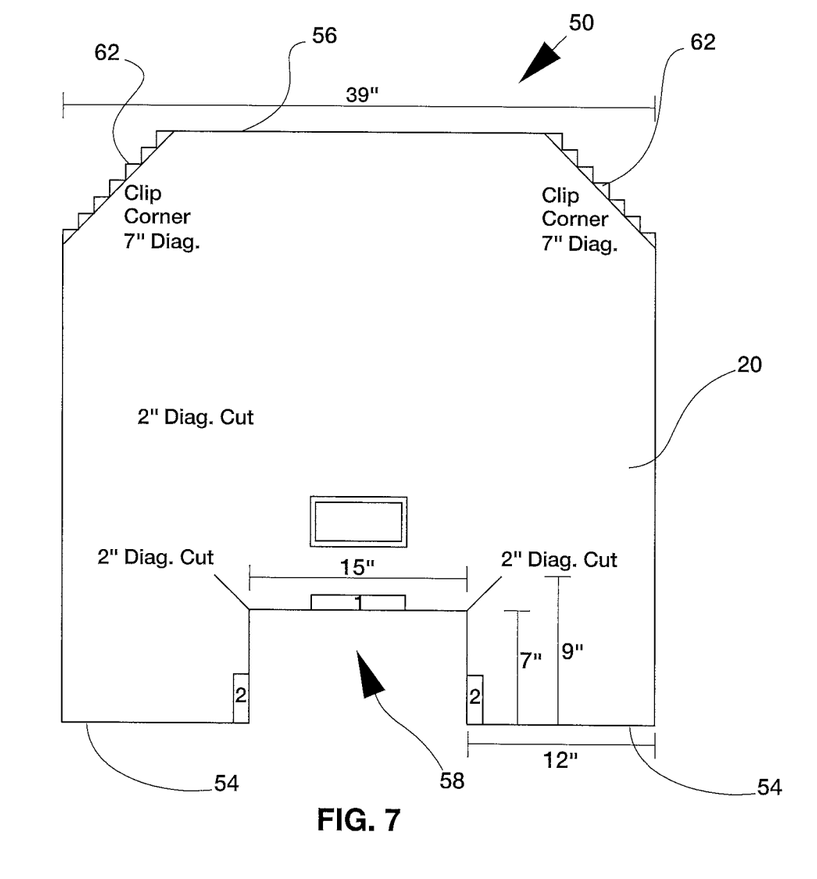
FIG. 7 is top view of another embodiment of an end drape according to the present disclosure.
Figure 8:
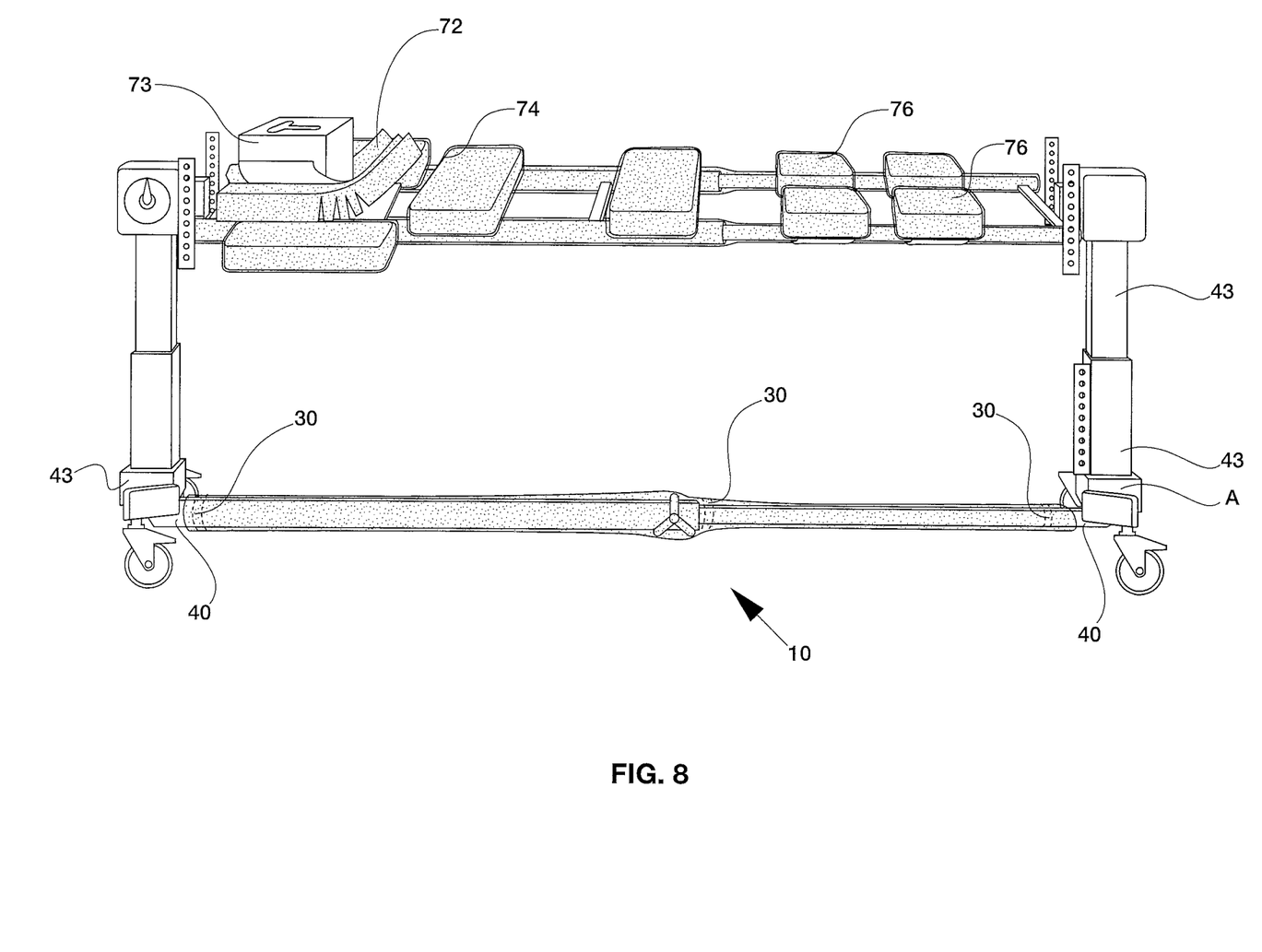
FIG. 8 is a side perspective view of one example of a clamping drape and drape system.
Figure 9:
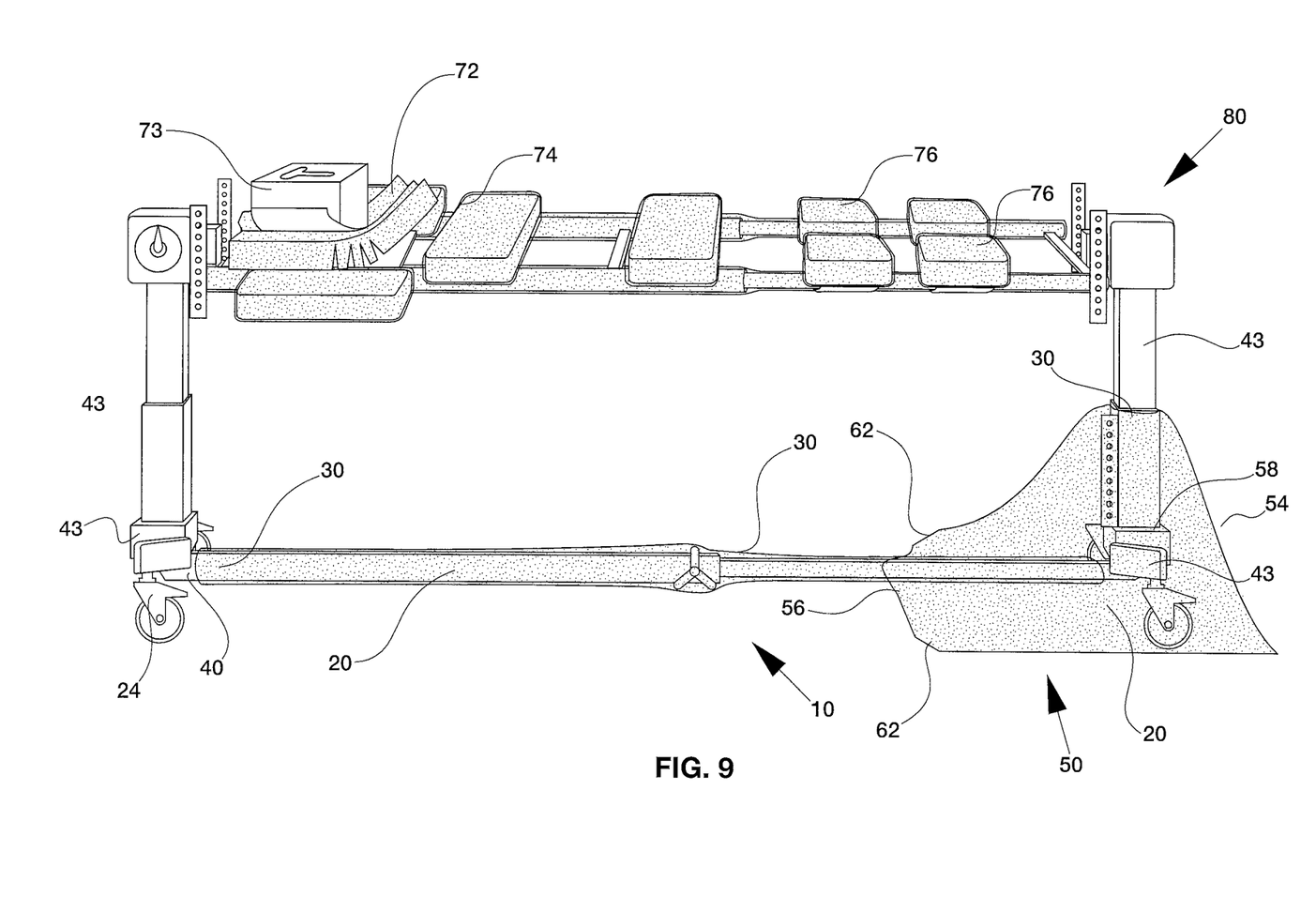
FIG. 9 is a side perspective view of one example of a clamping drape, end drape and a drape system and kit according to the present disclosure.

In yet other examples, an end drape 50 may include a table end 54 that secures to a table base end and a distal end 56 that extends away from the table base end 43. The table base end may include a cutout portion 58 that recesses into the end drape. The cutout 58 may be configured to surround and/or secure to a table base end 43. The cutout 58 may include an adhesive. The cutout 58 may include an adhesive around the perimeter of the cutout. The cutout 58 may include an adhesive along each side of the cutout. The cutout 58 may include diagonal cuts. The drape 50 may take on the characteristics and configurations of the other drapes disclosed herein. The drape 50 may include one or more clipped corners 62 at the distal end 56. The drape 50 may surround the table base end 43 such that cutout 58 wraps around the table base end 43 along its lower end or may also attach higher along the table base end to cover more and/or all of the equipment located at the table base end. The drape 50 may extend outwardly away from the table base end and away from the table. The drape 50 may extend outwardly away from the table base end 43 toward the table such that the distal end 56 terminates under the table. The drape 50 may overlap the drape 10 at the drape 50 distal end so the drape 10 and drape 50 form a continuous barrier under the medical table.

The end drape 50 may be an accessory drape for forming a kit including at least one self-clamping drape 10 and at least one accessory drape 50. The end drape 50, one example as shown in FIGS. 5, 6, and 7 may work with a self-clamping drape to cover end portions of a hard to fit and irregularly shaped medical table, such as the Jackson table show in FIG. 4. A kit may include a drape 10, a clamping system and an accessory drape 50.

In other examples, a drape kit may include a drape 10 having a clamping system. They kit may also include an end drape 50. The kit may include a set of end drapes, one for each end of the table 80. The kit may also include other accessory items, by way of example a chest pad cover 74, a hip/thigh cover 76, a foam headrest pillow 73, at least one foam arm cradle, all of these and/or in any combination.

The drape 10 including a clamping system allows for a speed application and the drape remains adjustable even after the first application and during the medical procedure. The drape 10 is length adjustable. The drape 10 is length adjustable without trimming or injuring the impervious surface of the drape.

A kit including any of the embodiments disclosed herein is considered within the scope of the inventions of the present disclosure.

A draping system including any of the embodiments disclosed herein is considered within the scope of the inventions of the present disclosure.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

I claim:

1. A disposable medical drape for containment of medical waste fluids, said drape comprising:

a flexible drape body having an impervious side and an absorbent side, a first drape end, a second drape end, a clamp for a first drape end, a clamp for a second drape end, and a clamp for in between the first and second drape ends attached to said drape, the clamps including a self-maintained first linear non-clamped position and a self-maintained non-linear, second-clamp position, wherein said clamps are adapted to alternate said drape between the self-maintained first linear non-clamped position, for adherence to a medical table base having a curved dimension, and the self-maintained non-linear, second-clamp position.

2. The disposable medical drape of claim 1 wherein said drape may include a position between the first non-clamped position and the second-clamp position.

3. The disposable medical drape of claim 1 wherein said drape is configured to self-clamp and maintain a clamped position about a circular base.

4. A self-clamping, disposable medical drape for containment of medical waste fluids, said drape comprising:

a flexible drape body having an impervious side and an absorbent side, a first drape end, a second drape end, at least one clamp, including a self-maintained first linear non-clamped position and a self-maintained non-linear, second-clamp position, wherein said at least one clamp is adapted to alternate said drape between the self-maintained first linear non-clamped position, for adherence to a medical equipment having a curved dimension, and the self-maintained non-linear, second-clamp position, wherein said self-clamping drape is configured to be in a first non-clamped position prior to installing said drape about a table base, the second clamp position when installed about a table base, and a releasable position configured to be removable from the table base when pulled away from the base.

5. The disposable medical drape of claim 1 wherein said drape includes a superabsorbent polymer for absorbing medical wastes.

6. The disposable medical drape claim 4 wherein the at least one clamp is attached to said drape and the clamp biases the drape to surround a base and maintain a position covering said base of a medical table.

7. The disposable medical drape of claim 4 wherein said drape is configured to be secured about a non-linear surface by the at least one clamp.

8. The disposable medical drape of claim 4 wherein said at least one clamp includes a first clamp end and a second clamp end, the clamp ends being distal from each other in the first non-clamped position and biased toward each other in the second clamped position.

9. The disposable medical drape of claim 4 including an accessory drape.

10. The disposable medical drape of claim 9 wherein said accessory drape is an end drape.

11. The disposable medical drape of claim 10 wherein said end drape includes:

an impervious side, an absorptive side, a table end configured to attach the end drape to a table end, a cutout portion in the table end; and a distal end configured to overlap with said disposable medical drape.

12. A disposable medical drape kit for containment of medical wastes, comprising:

a self-clamping, disposable medical drape configured to cover an equipment base of a medical table under a patient support, a set of end drapes configured to cover each base end of a medical table, wherein said medical drape and a distal drape end of each end drape overlaps under the patient support and forms a barrier covering the medical table portions below the patient support in order to protect the medical table portions below the patient support from medical waste exposure.

13. The disposable medical drape kit of claim 12 including an accessory drape.

14. A disposable medical drape for containment of medical waste fluids, said drape comprising:

a body portion, a first side portion, a second side portion, a first end, the first end being a table base end, a cut out in the first end, a second end, the second end being a distal end, wherein said drape is configured to create a barrier between fluids escaping a patient support and an irregularly shaped lower portion of a medical table below the patient support and toward the base, and wherein the cut out in the first end surrounds and attaches to a vertical portion of the base.

15. The drape of claim 14 including an adhesive at the cut out in the first end configured to secure the drape to an end of the table base.

16. The drape of claim 15 including a second self-clamping drape configured to clamp to a base below a patient support of a medical table, wherein the self-clamping drape and the drape overlap below the patient support.

\* \* \* \* \*